United States Patent [19]

Keys

[11] Patent Number: 5,670,472

[45] Date of Patent: Sep. 23, 1997

[54] BIODEGRADABLE ESTER DIQUATERNARY COMPOUNDS AND COMPOSITIONS CONTAINING THEM

[75] Inventor: Robert O. Keys, Columbus, Ohio

[73] Assignee: Witco Corporation, Greenwich, Conn.

[21] Appl. No.: 450,473

[22] Filed: May 26, 1995

Related U.S. Application Data

[63] Continuation-in-part of Ser. No. 230,319, Apr. 19, 1994, abandoned.

[51] Int. Cl.$^6$ .................. D06M 10/08; C07C 229/26
[52] U.S. Cl. .................. 510/433; 510/434; 510/480; 510/490; 510/504; 510/505; 510/519; 510/521; 554/107
[58] Field of Search .................. 252/8.6, 8.8, 8.9, 252/547, 546; 554/107; 510/504, 505, 433, 434, 490, 477, 480, 515, 519, 521

[56] References Cited

U.S. PATENT DOCUMENTS

| | | | |
|---|---|---|---|
| 2,226,116 | 12/1940 | Groote et al. | 260/404 |
| 2,228,988 | 1/1941 | Groote et al. | 260/404 |
| 2,828,262 | 3/1958 | Morway | 252/33.6 |
| 2,878,144 | 3/1959 | Conbere et al. | 117/139.5 |
| 2,980,673 | 4/1961 | Hidalgo et al. | 260/247.2 |
| 3,095,373 | 6/1963 | Blomfield et al. | 252/8.8 |
| 3,170,938 | 2/1965 | Levis | 260/404.5 |
| 3,299,138 | 1/1967 | Sveum | 260/567.6 |
| 3,442,692 | 5/1969 | Gaiser et al. | 117/120 |
| 3,578,697 | 5/1971 | Marans | 260/465.4 |
| 3,634,947 | 1/1972 | Furgal | 34/60 |
| 3,676,199 | 7/1972 | Hewitt et al. | 117/109 |
| 3,686,025 | 8/1972 | Morton et al. | 117/140 R |
| 3,936,503 | 2/1976 | Miller et al. | 260/567.6 P |
| 4,067,689 | 1/1978 | Perrier et al. | 8/129 |
| 4,128,485 | 12/1978 | Bauman et al. | 252/8.8 |
| 4,251,380 | 2/1981 | Hammond et al. | 252/34 |
| 4,273,663 | 6/1981 | Hammond et al. | 252/34 |
| 4,277,350 | 7/1981 | Minegishi et al. | 252/8.8 |
| 4,313,889 | 2/1982 | Boder | 260/404 |
| 4,339,391 | 7/1982 | Hoffmann et al. | 260/401 |
| 4,364,741 | 12/1982 | Villa | 44/51 |
| 4,561,998 | 12/1985 | Wertz et al. | 252/547 |
| 4,631,071 | 12/1986 | Axelrod et al. | 44/71 |
| 4,639,256 | 1/1987 | Axelrod et al. | 44/71 |
| 4,640,954 | 2/1987 | Schnee et al. | 524/516 |
| 4,701,268 | 10/1987 | Nelson et al. | 252/8.8 |
| 4,767,547 | 8/1988 | Straathof et al. | 252/8.8 |
| 4,808,321 | 2/1989 | Walley | 252/8.8 |
| 4,880,430 | 11/1989 | Schleusener | 8/188 |
| 4,882,917 | 11/1989 | Mizusawa et al. | 68/17 A |
| 4,906,413 | 3/1990 | Topfl et al. | 260/404.5 |
| 4,939,289 | 7/1990 | Oxenrider et al. | 560/87 |
| 5,081,293 | 1/1992 | Borland et al. | 562/575 |
| 5,105,008 | 4/1992 | Sauer et al. | 562/575 |
| 5,128,053 | 7/1992 | Gummo et al. | 252/8.6 |
| 5,183,580 | 2/1993 | Lew et al. | 252/8.6 |
| 5,194,667 | 3/1993 | Oxenrider et al. | 560/87 |
| 5,468,398 | 11/1995 | Farooq et al. | 252/8.8 |
| 5,476,598 | 12/1995 | Schramm, Jr. et al. | 252/8.8 |

FOREIGN PATENT DOCUMENTS

| | | |
|---|---|---|
| 645855 | 7/1962 | Canada . |
| 0 199 382 | 10/1986 | European Pat. Off. . |
| 652361 | 1/1965 | France . |
| 3127239 | 1/1983 | Germany . |
| 331118 | 12/1993 | Japan . |
| 212567 | 8/1994 | Japan . |
| 256272 | 9/1994 | Japan . |
| 340598 | 12/1994 | Japan . |
| 18570 | 1/1995 | Japan . |
| 18571 | 1/1995 | Japan . |
| 94/14938 | 7/1994 | WIPO . |

Primary Examiner—Douglas J. McGinty
Assistant Examiner—John R. Hardee
Attorney, Agent, or Firm—Scully, Scott, Murphy & Presser

[57] ABSTRACT

Disclosed are compounds of the formula (I)

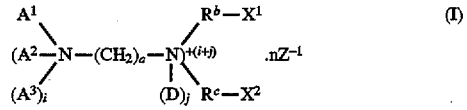

useful as fabric softening compounds which exhibit enhanced biodegradability.

25 Claims, No Drawings

BIODEGRADABLE ESTER DIQUATERNARY COMPOUNDS AND COMPOSITIONS CONTAINING THEM

This application is a continuation-in-part of prior application Ser. No. 08/230,319, filed Apr. 19, 1994, now abandoned.

The present invention relates to compositions and processes for treating fabrics in the rinse cycle of an automatic clothes washer, or in an automatic laundry dryer, to provide static control and softening.

BACKGROUND OF THE INVENTION

Fabrics can be treated to impart softness, static control and antistatic properties by addition of fabric softening compositions to the rinse cycle, as part of the detergent system, or in the automatic clothes drying cycle of the standard washing and drying routine. Treatment in the rinse cycle of washing machines and in clothes dryers has been shown to be an effective means for applying softening compositions to textiles.

Various chemical compositions have been used commercially for softening fabrics when applied during the laundering operation. This softening or conditioning is normally understood and results in a smooth, fluffy feel to the touch. The most common softening compositions include one or more quaternary ammonium salts. Among the most commercially attractive are imidazolinium sales, imadizoline salts, dimethyl dialkyl quaternary salts, and diamidoamine quaternary salts. The majority of these compounds are derived from fatty raw materials, and these cationics have been the subject of many innovations. See, for example, U.S. Pat. Nos. 3,634,947; 3,686,025; 3,095,373 and 3,442,692. Disclosures specifically for dryer-added fabric softeners include U.S. Pat. No. 3,676,199. In all of the commercially used dryer-softener systems there is included from 10–30% of a release agent to accomplish the transfer of the active softener to the textile being dried. This requirement for the release agent results in additional handling and manufacturing costs.

It is, therefore, an object of the present invention to provide a material for the treatment of textiles in a washing machine or in an automatic dryer to provide softness and static control to the fabric with improved transfer properties to the fabric.

It is an additional objective of the present invention to provide a softening system for use in washers and/or in dryers comprising a softener exhibiting faster biodegradation than currently available systems.

The present invention relates to certain diquaternary diesters to provide good softening and antistatic properties while exhibiting excellent transfer to the clothes, combined with a high degree of biodegradability.

BRIEF SUMMARY OF THE INVENTION

One aspect of the present invention is a composition of the formula (I):

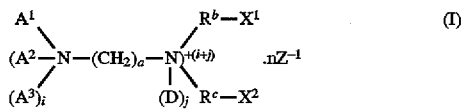

wherein $A^1$, $A^2$ and $A^3$ are the same or different and each is alkyl containing up to 3 carbon atoms, benzyl, or H—(Alk—O)$_{1-3}$—Alk— wherein Alk signifies —CH$_2$CH$_2$—, —CH(CH$_3$)CH$_2$—, or —CH$_2$CH(CH$_3$)—, provided further that $A^1$ can be —(CH$_2$)$_{1-3}$COO$^-$, and $A^3$ can be hydrogen;

$R^b$ is —(CH$_2$)$_b$— or —Alk—(O—Alk)$_{2-6}$—;
$R^c$ is —(CH$_2$)$_c$— or —Alk—(O—Alk)$_{2-6}$—;
a is 2 to 6;
b is 2 to 4;
c is 2 to 4;
D is methyl, ethyl, propyl, —(CH$_2$)$_{1-3}$COO$^-$, benzyl or hydrogen;
i is 0 or 1 and j is 0 or 1, provided that the sum of (i+j) is 1 or 2;
$X^1$ and $X^2$ are independently YC(O)O— or YOC(O)— wherein Y is a straight or branched saturated or unsaturated aliphatic group containing up to 3 carbon-carbon double bonds and containing 11 to 23 carbon atoms;
n is (two minus the number of —(CH$_2$)$_{1-3}$COO$^-$ substituents present); and
Z is an anion.

Another aspect of the present invention is a method of imparting softening or antistatic properties to fabric by contacting the fabric with an effective amount of one or more compounds corresponding to the above formula (I).

Additional aspects of the present invention include articles and compositions containing one or more compounds of formula (I) in a form useful in imparting softening and/or antistatic to fabrics. For instance, compounds of this invention can be disposed in an effective manner into an automatic dryer under conditions which provide for release of an effective amount of the composition onto the fabrics. Normally, softening compositions are deposited on an absorbent substrate as an impregnate or as a coating. Alternatively, compounds of this invention can be formulated into liquid preparations, optionally also including one or more of detergents, optical brighteners, and soil release agents, and the like, whereupon the softening compound or compounds of formula (I) can be added into an automatic clothes washing machine, generally in the rinse cycle.

DETAILED DESCRIPTION OF THE INVENTION

With reference to formula (I), the substituents $A^1$, $A^2$ and $A^3$ may be the same or different and are preferably the same for ease of synthesis. Each of $A^1$, $A^2$ and $A^3$ can be alkyl containing up to 3 carbon atoms, such as methyl, ethyl, n-propyl or isopropyl. Preferably, $A^1$, $A^2$ and $A^3$ are each methyl. One or more of these three substituents may be benzyl or may correspond to the formula H—(Alk—O)$_{1-3}$—Alk— wherein Alk signifies ethylene or isopropylene, that is, —CH$_2$CH$_2$—, —CH(CH$_3$)CH$_2$—, or —CH$_2$CH(CH$_3$)—.

The substituent $A^1$, that is, one of the substituents on the nitrogen to which $A^1$, $A^2$ and $A^3$ are attached, can also be a betaine-type substituent of the formula —CH$_2$COO$^-$, —(CH$_2$)$_2$COO$^-$ or —(CH$_2$)$_3$COO$^-$. In addition, the substituent $A^3$ can be hydrogen, as can the substituent D.

It will be recognized from the definitions of the subscripts i and j that one or both of the nitrogen atoms in the compounds of formula (I) are tetra-substituted and will, therefore, carry a positive charge. The positive charge, whether +1 or +2, is balanced by the presence of anions X$^-$, by the "internal salt" afforded by the presence of —(CH$_2$)$_{1-3}$COO$^-$ substituents, or by any combination of X$^-$ and —(CH$_2$)$_{1-3}$COO$^-$ presence.

Referring again to formula (I), the chain lengths defined by the subscripts a, b and c are selected to optimize the fabric softening properties of the compound. Thus, a is 2 to 6, and preferably 2, 3 or 4. Likewise, b and c are each 2, 3 or 4, and each is preferably 2. The substituent D can be a substituent, such as hydrogen, methyl, ethyl, n-propyl, isopropyl, benzyl, or —$(CH_2)_{1-3}COO^-$. Preferably, D is hydrogen or methyl or ethyl.

The substituents $X^1$ and $X^2$ are derived from natural or synthetic long-chain fatty acids preferably containing 12 to 24 carbon atoms. Such fatty acids can be straight or branched and saturated or unsaturated. Typically, when unsaturated fatty acids are used, they may contain one, two or three carbon-carbon double bonds. The chain lengths of the substituents $X^1$ and $X^2$ are selected with reference to the desired final properties, including solubility, melting point and ease of application onto a fabric substrate in the preparation of a fabric softening sheet for use in a clothes dryer.

The anion Z can be any conventional organic or inorganic anion compatible with the fabric softening properties of the compound and with the other components with which the fabric softener may be used, such as detergent, bleach and so forth. Preferably, Z is chloride, bromide, methylsulfate, or ethylsulfate. The anion can be monovalent or divalent and is preferably monovalent for solubility purposes. There must be a sufficient amount of the anion present to balance the net charge of the rest of the compound. Thus, the number of moles of anion per mole of diquaternary is two minus the number of betaine-type substituents —$(CH_2)_{1-3}COO^-$.

Compounds in accordance with formula (I) are made by straightforward techniques employing readily available starting materials. For instance, a compound of the formula $(A^1)(A^2)N$—$(CH_2)_a$—$NH_2$ is di-alkoxylated on the unsubstituted nitrogen by reaction with one molar equivalent each of compounds of the formula L—$(CH_2)_b$—OH and L—$(CH_2)_a$—OH (or two molar equivalents of L—$(CH_2)_b$OH where it is desired that b and c are to be equal) where L is a suitable leaving group such as chloro. Alternatively, the compound of the formula $(A^1)(A^2)N$—$(CH_2)_a$—$NH_2$ is reacted on the unsubstituted nitrogen with a total of 2 moles or more of one or more compounds of the formula L—Alk—(O—Alk)$_{2-6}$—OH. The resulting bis(hydroxyalkylene)-substituted or bis(hydroxy-polyalkoxy)-substituted diamine is then reacted with two molar equivalents of fatty acid, that is, a total of two molar equivalents of one or more fatty acids of the formula Y—COOH wherein Y is as described above. The resulting diester compound can then be quaternized or protonated at one or both nitrogens by reaction under conventional quaternization conditions with quaternization agents such as methyl chloride, dimethyl sulfate, and the like, or by protonation with a suitable strong acid of the formula HX.

In the case where the desired compounds are substituted with YOC(O)— groups instead of long chain acyloxy radicals, the synthesis proceeds through the formation of a diacid intermediate which is subsequently esterified with the corresponding fatty alcohol Y—OH.

The preferred compounds of the present invention are disubstituted as YC(O)O—.

When it is desired to provide one or two substituents of the formula —$CH_2COO^-$, —$(CH_2)_2COO^-$ or —$(CH_2)_3COO^-$, the appropriate intermediate is reacted after esterification with a reactive acid L—$CH_2COOH$, L—$(CH_2)_2COOH$ or L—$(CH_2)_3COOH$ where L is a suitable leaving group. Preferred reactants for this step are chloroacetic acid or chloropropionic acid.

Compounds of the present invention exhibit a number of advantages making them particularly advantageous for use in the fabric softening applications. For instance, the synthesis of these compounds does not generate byproduct salts, thereby alleviating the need to remove byproducts during manufacture and thereby alleviating the burdens of waste disposal. In addition, the compounds can be synthesized in a straight-forward manner not requiring extra steps or posing any unusual or difficult reaction conditions. In particular, avoiding the need to recover byproduct salts affords rapid attainment of product in high yield, without the additional steps that would be entailed if salts were present that had to be removed.

In addition, the compounds of formula (I) would exhibit enhanced biodegradability, thereby permitting the use of fabric softening compositions and articles even under circumstances where relatively stringent controls need to be implemented on the volume and content of waste water effluent streams. This biodegradability also contributes to the lessening of the burden on household and municipal waste water treatment facilities.

The compounds of the present invention are preferably used by providing them to the fabric to be softened in amounts effective to afford softening or antistatic properties to the fabric. Satisfactory amounts typically range from 1 to 2 grams of softening compound(s) per load of laundry. When the mode in which the compound is to be provided is a solid article, it is typically prepared by coating the compound or compound(s) per se onto a solid carrier such as a suitably sized swatch of woven or non-woven fabric such as spun, bonded polyester sheet. The sheets are provided in any of the conventional means such as a pop-up dispenser or a roll of perforated sheets, whereby the user can remove a single sheet and add it to the load of laundry in the automatic clothes dryer. Alternatively, the fabric softening compounds of the present invention can be provided in a liquid or solid formulation. In the liquid formulation, the softener compound is suspended and/or dissolved in water optionally containing as well other ingredients and diluents such as detergents, viscosity builders, optical brighteners, salt release agents, water, fragrance, and so forth, in relative amounts effective to provide about 1 to about 2 grams of fabric softening compound in the dose of the liquid composition which is added to the load of fabric being washed. In the solid formulation, the product comprises small flowable solid particles or beads on a water-soluble carrier such as solid detergent optionally compounded with builders, brighteners, fragrance, and the like as is known in the art.

Preferred compounds within the scope of the present invention include the following:

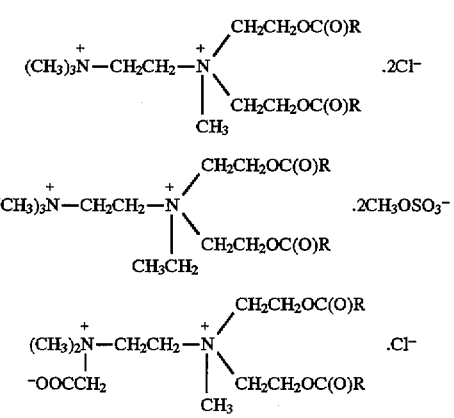

-continued $$(CH_3)_2\overset{+}{N}H-CH_2CH_2-\overset{+}{N}H\diagdown^{CH_2CH_2OC(O)R}_{CH_2CH_2OC(O)R} \quad .2CH_3CH_2OSO_3^-$$

R = tallow, hydrogenated tallow, stearyl, or coco radical

What is claimed is:

1. A compound of the formula (I)

$$\begin{array}{c}A^1\diagdown\qquad\qquad R^b-X^1\\(A^2-N-(CH_2)_a-N)^{+n}\qquad .nZ^{-1}\\(A^3)_i\qquad\quad(D)_j\quad R^c-X^2\end{array}\qquad(I)$$

wherein $A^1$, $A^2$ and $A^3$ are the same or different and each is alkyl containing up to 3 carbon atoms, benzyl, or H—(Alk—O)$_{1-3}$—Alk— wherein Alk signifies —CH$_2$CH$_2$—, —CH(CH$_3$)CH$_2$—, or —CH$_2$CH(CH$_3$)—, provided further that $A^1$, can be —(CH$_2$)$_{1-3}$COO$^-$ and that $A^3$ can be hydrogen;

$R^b$ is —Alk—(O—Alk)$_{2-6}$;

$R^c$ is —Alk—(O—Alk)$_{2-6}$;

a is 2 to 6;

D is methyl, ethyl, propyl, —(CH$_2$)$_{1-3}$COO$^-$, or benzyl;

i is 0 or 1 and j is 1, provided that the sum of (i+j) is 1 or 2; and provided that if i is 0 then $A^1$ and D cannot both be —(CH$_2$)$_{1-3}$COO—;

$X^1$ and $X^2$ are independently YC(O)O— or YOC(O)— wherein Y is a straight or branched saturated or unsaturated aliphatic group containing up to 3 carbon-carbon double bonds and containing 11 to 23 carbon atoms;

n is ((i+j) minus the number of —(CH$_2$)$_{1-3}$COO$^-$ substituents present); and Z is an anion.

2. A compound in accordance with claim 1 wherein $A^1$, $A^2$ and $A^3$ are the same or different and each is alkyl containing up to 3 carbon atoms.

3. A compound according to claim 2 wherein $A^1$, $A^2$ and $A^3$ are methyl.

4. A compound in accordance with claim 1 wherein a is 2 to 4.

5. A compound in accordance with claim 1 wherein D is hydrogen or methyl.

6. A compound in accordance with claim 1 wherein $X^1$ and $X^2$ have the formula YC(O)O— wherein Y is a straight or branched saturated or unsaturated aliphatic group containing from zero up to 3 carbon-carbon double bonds and containing 11 to 23 carbon atoms.

7. A compound in accordance with claim 1 wherein Z is chloride, bromide, methylsulfate or ethylsulfate.

8. A compound in accordance with claim 1 wherein $A^1$, $A^2$, $A^3$ and D are each methyl.

9. A compound in accordance with claim 1 wherein one or both of $A^1$ and D are —(CH$_2$)$_{1-3}$COO$^-$.

10. A solid composition useful as a fabric softener comprising a fabric softening and antistatic effective amount of at least one compound in accordance with claim 1.

11. A liquid composition useful as a fabric softener comprising a fabric softening and antistatic effective amount of at least one compound in accordance with claim 1.

12. A method of imparting fabric softening to fabric, comprising contacting the fabric with a fabric softening and antistatic effective amount of one or more compounds in accordance with claim 1.

13. A compound of the formula $$\begin{array}{c}A^1\diagdown\qquad\qquad R^b-X^1\\(A^2-N-(CH_2)_a-N)^{+n}\qquad .nZ^{-1}\\(A^3)_i\qquad\quad(D)_j\quad R^c-X^2\end{array}\qquad(I)$$

wherein $A_1$, $A_2$ and $A_3$ are the same or different and each is alkyl containing up to 3 carbon atoms, benzyl or H—(Alk—O)$_{1-3}$—Alk— wherein Alk signifies —CH$_2$CH$_2$—, —CH(CH$_3$)CH$_2$—, or —CH$_2$CH(CH$_3$)—, provided further that $A^1$ can be —(CH$_2$)$_{1-3}$COO$^-$ and that $A^3$ can be hydrogen;

$R^b$ is —(CH$_2$)$_b$—;

$R^c$ is —(CH$_2$)$_c$—;

a is 2 to 6;

b is 2 to 4;

c is 2 to 4;

D is methyl, ethyl, propyl, —(CH$_2$)$_{1-3}$COO$^-$, benzyl or hydrogen;

i is 0 or 1 and j is 0 or 1, provided that the sum of (i+j) is 1 or 2; and provided that if i is zero then D is not hydrogen, if j is zero then $A^3$ is not hydrogen, and if i and j are both one then one or both of $A^3$ and D are not hydrogen; and provided further that if i is zero then $A^1$ and D cannot both be —(CH$_2$)$_{1-3}$COO$^-$;

$X^1$ and $X^2$ are independently YC(O)O— or YOC(O)— wherein Y is a straight or branched saturated or unsaturated aliphatic group containing up to 3 carbon-carbon double bonds and containing 11 to 23 carbon atoms;

n is ((i+j) minus the number of —(CH$_2$)$_{1-3}$COO$^-$ substituents present); and Z is an anion.

14. A compound in accordance with claim 13 wherein $A^1$, $A^2$ and $A^3$ are the same or different and each is alkyl containing up to 3 carbon atoms.

15. A compound according to claim 14 wherein $A^1$, $A^2$ and $A^3$ are methyl.

16. A compound in accordance with claim 13 wherein a is 2 to 4.

17. A compound in accordance with claim 13 wherein a is 2, b is 2 and c is 2.

18. A compound in accordance with claim 13 wherein D is hydrogen or methyl.

19. A compound in accordance with claim 13 wherein $X^1$ and $X^2$ have the formula YC(O)O— wherein Y is a straight or branched saturated or unsaturated aliphatic group containing from zero up to 3 carbon-carbon double bonds and containing 11 to 23 carbon atoms.

20. A compound in accordance with claim 13 wherein Z is chloride, bromide, methylsulfate or ethylsulfate.

21. A compound in accordance with claim 13 wherein $A^1$, $A^2$, $A^3$ and D are each methyl, and a, b and c are each 2.

22. A compound in accordance with claim 13 wherein one or both of $A^1$ and D are —(CH$_2$)$_{1-3}$COO$^-$.

23. A solid composition useful as a fabric softener comprising a fabric softening and antistatic effective amount of at least one compound in accordance with claim 13.

24. A liquid composition useful as a fabric softener comprising a fabric softening and antistatic effective amount of at least one compound in accordance with claim 13.

25. A method of imparting fabric softening to fabric, comprising contacting the fabric with a fabric softening and antistatic effective amount of one or more compounds in accordance with claim 13.

* * * * *